United States Patent [19]

Niess

[11] 3,981,883

[45] Sept. 21, 1976

[54] MANUFACTURE OF 3-AMINO-2,1-BENZISOTHIAZOLES

[75] Inventor: Rolf Niess, Schifferstadt, Germany

[73] Assignee: BASF Aktiengesellschaft, Ludwigshafen (Rhine), Germany

[22] Filed: Mar. 6, 1975

[21] Appl. No.: 556,155

[30] Foreign Application Priority Data

Mar. 18, 1974 Germany............................ 2412975

[52] U.S. Cl............................ 260/304 A; 260/558 S
[51] Int. Cl.²........................................ C07D 277/60
[58] Field of Search................................ 260/304 A

[56] References Cited
FOREIGN PATENTS OR APPLICATIONS
1,445,547   12/1968   Germany........................ 260/304 A Primary Examiner—Nicholas S. Rizzo
Assistant Examiner—D. B. Springer
Attorney, Agent, or Firm—Johnston, Keil, Thompson & Shurtleff

[57] ABSTRACT

Process for the manufacture of 3-amino-2,1-benzisothiazoles by oxidative ring closure of o-aminothiobenzamides, comprising the improvement of conducting the reaction in about 85 to 110% sulfuric acid which serves as solvent and oxidizing agent. 3-Amino-2,1-benzisothiazoles are important diazo components for blue azo dyes.

10 Claims, No Drawings

MANUFACTURE OF 3-AMINO-2,1-BENZISOTHIAZOLES

German Published Application No. 1,445,547 describes a process for the manufacture of this class of compounds, wherein o-amino-thiobenzamides, in solution or suspension, are subjected to oxidative ring closure by means of suitable oxidizing agents. It has now proved possible, surprisingly, to simplify and improve the above process.

We have found that 3-amino-2,1-benzisothiazoles of the formula I

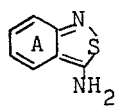   I in which the ring A may be substituted, can be manufactured particularly advantageously from compounds of the formula II

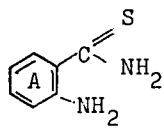   II by oxidative ring closure, if the ring closure is carried out in about 85 to 110% strength sulfuric acid at from about 10° to 160°C, optionally with the addition of an oxidizing agent.

The compounds of the formula II, i.e. o-aminothiobenzamides or anthranilic acid thioamides, are easily obtainable, e.g., by reaction of o-aminobenzonitriles with hydrogen sulfide in the presence of ammonia. with a particular view to further conversion of the 3-amino-2,1-benzisothiazoles to dyes, suitable anthranilic acid thioamide starting materials for the process according to the invention contain halogen, especially chlorine and bromine, alkyl of 1 to 12 carbon atoms, preferably of 1 to 4 carbon atoms, such as methyl, ethyl, propyl, isopropyl or butyl, aralkyl (e.g. benzyl), aryl (e.g. phenyl), nitro, amino, mono- or di-alkyl (e.g. $C_{1-14}$ alkyl)-substituted or -aryl (e.g. phenyl) substituted amino, acyl (e.g. acetyl, benzoyl), hydroxyl, alkoxy (e.g. methoxy, ethoxy), aryloxy (e.g. phenoxy), sulfonamide (e.g. sulfamoyl, $C_{1-14}$-alkyl, mono- or di-substituted sulfamoyl, phenylsulfamoyl), alkylsulfonyl (e.g. methylsulfonyl, ethylsulfonyl) or arylsulfonyl (e.g. phenylsulfonyl) as substituents in the ring A. The preferred substituents are chlorine, bromine and nitro.

The following compounds may be mentioned as examples: anthranilic acid thioamide, 5-methylanthranilic acid thioamide, 6-ethylanthranilic acid thioamide, 3,6-dimethylanthranilic acid thioamide, 6-methoxyanthranilic acid thioamide, 3-chloroanthranilic acid thioamide, 4-chloroanthranilic acid thioamide, 5-chloroanthranilic acid thioamide, 6-chloroanthranilic acid thioamide, 3,5-dichloroanthranilic acid thioamide, 3,4,5,6-tetrachloroanthranilic acid thioamide, 3-bromoanthranilic acid thioamide, 4-bromoanthranilic acid thioamide, 5-bromoanthranilic acid thioamide, 6-bromoanthranilic acid thioamide, 3,5-dibromoanthranilic acid thioamide, 3,4,6-tribromoanthranilic acid thioamide, 3,4,5,6-tetrabromoanthranilic acid thioamide, 3-nitroanthranilic acid thioamide, 5-nitroanthranilic acid thioamide, 6-nitroanthranilic acid thioamide, 3,5-dinitroanthranilic acid thioamide, 3-chloro-5-nitroanthranilic acid thioamide, 3-bromo-5-nitroanthranilic acid thioamide and 5-aminoanthranilic acid thioamide.

The process is expediently carried out by introducing the thioamide into the concentrated sulfuric acid, advantageously whilst stirring the mixture. The unexpected advantage of using sulfuric acid as the solvent is, inter alia, that this acid at the same time acts as the oxidizing agent for the oxidative ring closure. The concentration of the sulfuric acid used is suitably from 85 to 110% and preferably from 95 to 102%. The concentration of the sulfuric acid must be so chosen that no sulfonation occurs; this means that for thioamides with substituents, e.g. nitro, which make sulfonation more difficult, the concentration can be higher than for thioamides which contain substituents, e.g. alkyl or alkoxy, which assist the sulfonation.

The temperature range within which the reaction can be carried out depends on the concentration and is from 10° to 160°C, preferably from 40° to 90°C. The duration of the reaction depends both on the concentration of the sulfuric acid and on the reaction temperature and is from 10 minutes to 10 hours. The reaction is particularly advantageously carried out with from 96 to 100% strength sulfuric acid at a temperature of from 60° to 100°C, which is maintained for from 1 to 5 hours. It is advantageous to pass a gas through the reaction mixture during the reaction to remove the sulfur dioxide. The amount of sulfuric acid used is suitably chosen in accordance with the solubility characteristics of the reactants and should be such that the components are in solution, though the reaction can also be carried out with a suspension of the thioamide in sulfuric acid. Preferably, the amount by weight of sulfuric acid is from 3 to 15 times the amount by weight of the thioamide.

The reaction is exothermic and its start is shown by the rise in temperature and by the evolution of sulfur dioxide. The start can be accelerated by heating, eg. by means of a bath. For example, the mixture can be heated to 50°C, until the evolution of sulfur dioxide starts, and can then be kept at about 80°C for from 1 to 5 hours. The course of the reaction can be followed by analytical methods, eg. by thin layer chromatography. As soon as all the thioamide has been consumed, the sulfuric acid solution can be cooled, poured into ice water and be neutralized with bases, eg. potassium hydroxide, sodium hydroxide or ammonia. The 3-amino-2,1-benzisothiazoles separate out as solids, in almost quantitative yield, and can be isolated by conventional methods, eg. by filtration or centrifuging.

The oxidative ring closure can also be accelerated by adding oxidizing agents, in particular those described in German Published Application No. 1,445,547, or compounds which are converted into oxidizing agents by concentrated sulfuric acid. The advantage of this variant is that it requires a lower reaction temperature. Individual examples of oxidizing agents which may be used are hydrogen peroxide, peracetic acid, perbenzoic acid, perphthalic acid, sulfuryl chloride or bromine; the latter may also be used in the form of bromides. In this variant, it is possible either to dissolve or suspend the thioamide in sulfuric acid and add the oxidizing agent, whilst stirring, or first to introduce the oxidizing agent into sulfuric acid and then to introduce the thioamide, whilst stirring. The reaction is in these cases suitably carried out at from 10° to 60°C, advantageously at from 20° to 45°C. In the case of substances which are reoxidized by sulfuric acid under the reaction conditions, catalytic amounts suffice, whilst in other cases it is desirable to use equivalent amounts of thioamide and oxidizing agent.

A further advantage of the process according to the invention is that the resulting solutions of the 3-amino-2,1-benzisothiazoles in sulfuric acid can be diazotized directly, without intermediate isolation of the 3-amino-2,1-benzisothiazoles - and then be converted to azo dyes by coupling. Eg., as soon as the thioamide has been converted quantitatively, the sulfuric acid solution may be cooled to about 0°C and diazotized by conventional methods with sodium nitrite or with a solution of nitrosylsulfuric acid in concentrated sulfuric acid.

This is then followed by a conventional coupling reaction.

The parts in the Examples are by weight and bear the same relation to parts by volume as the kilogram to the liter.

EXAMPLE 1

15.5 parts of 3,5-dibromoanthranilic acid thioamide are added in portions, whilst stirring, to 200 parts of concentrated sulfuric acid which has been heated to 40°C. The temperature is slowly raised to 80°C (during which the evolution of sulfur dioxide starts) and is maintained at this level until starting material is no longer detectable by thin layer chromatography. After about 2 hours, the mixture is cooled, poured into 600 parts of ice water and brought to pH 5–6 with aqueous sodium hydroxide solution. The precipitated product is filtered off, washed with water and dried. 14.8 parts (97.5% of theory) of 5,7-dibromo-3-amino-2,1-benzisothiazole, melting at from 206° to 220°C, are obtained. A sample recrystallized from toluene melts at from 220° to 222°C.

EXAMPLE 2

49.25 parts of 5-nitro-2-aminobenzoic acid thioamide are introduced in portions, whilst stirring, into 450 parts of 100% strength sulfuric acid at room temperature. An exothermic reaction takes place and the temperature rises to 40°–50°C. After all the thioamide has been added, the temperature is raised slowly until the evolution of sulfur dioxide starts at from 60° to 70°C. The mixture is maintained at from 60° to 70°C for 2 hours and is then heated to 100°C for 1 hour. The solution is then cooled, poured into 1,000 parts of ice water and brought to pH 5–6 with aqueous sodium hydroxide solution. The precipitate is filtered off, washed with water and dried. 47.2 parts (96% of theory) of 3-amino-5-nitro-2,1-benzisothiazole, having a decomposition point in excess of 250°C, are obtained.

EXAMPLE 3

9.85 parts of 5-nitro-2-aminobenzoic acid thioamide are introduced, whilst stirring, into 110 parts of 100% strength sulfuric acid at room temperature; during this addition, the temperature rises to about 50°C and the mixture is then heated to from 60° to 70°C, during which sulfur dioxide gas is evolved. The temperature is now kept at 80°C for 5 hours and during this time air is drawn through the reaction mixture. After cooling to 0°C, 50 parts of an acetic acid/propionic acid mixture are added dropwise, followed by 14.5 parts of nitrosylsulfuric acid (containing 13.1% of free dinitrogen trioxide), also added dropwise. The resulting diazo solution is stirred for 3 hours at from 0° to 5°C and is then allowed to run into a solution of 9.8 parts of N,N-di-($\beta$-hydroxyethyl)-3-methylaminobenzene, 500 parts of water, 3 parts of concentrated hydrochloric acid and 250 parts of ice. The dye, obtained in a crystalline form, is filtered off, washed neutral with water and dried under reduced pressure at 50°.

The dye thus obtained dyes polyethylene glycol terephthalate in navy hues.

EXAMPLE 4

9.85 parts of 5-nitro-2-aminobenzoic acid thioamide are introduced, whilst stirring, into 110 parts of 100% strength sulfuric acid at room temperature, and after the initially exothermic reaction has subsided the mixture is heated for 5 hours to 80°C whilst constantly passing air through it. The resulting solution of 5-nitro-3-amino-2,1-benzisothiazole is first cooled, 16 parts of ice and 10 parts of propionic acid are added and the product is then diazotized at from 0° to 5°C with 15 parts of nitrosylsulfuric acid (containing 12.8% of free dinitrogen trioxide). The resulting diazo solution is stirred for 3 hours at from 0° to 5°C and 12.1 parts of 85.7% pure N-$\beta$-carbomethoxyethyl-N-ethylaniline (corresponding to 10.6 parts of 100% pure material) are added at from −5° to 0°C. The resulting mixture is then introduced into a solution of 130 parts of sodium formate and 0.5 part of amidosulfonic acid in 185 parts of water and 500 parts of ice at from −5° to 0°C and the batch is stirred for 1 hour at from −3 to 0°C. The dye, obtained in a crystalline form, is filtered off, washed neutral with water and dried at 50°C under reduced pressure. Yield, 16.5 parts (= 82% of theory), based on 5-nitro-2-aminobenzoic acid thioamide; melting point from 84 to 87°C.

EXAMPLE 5

7.75 parts of 2-amino-3,5-dibromobenzoic acid thioamide are introduced, whilst stirring, into 70 parts of 100% strength sulfuric acid at room temperature and the reaction mixture is heated to 90°C for 2 hours, whilst passing air through it. The solution is then cooled, 20 parts of a glacial acetic acid/propionic acid mixture (17:3) are added dropwise at from 0° to 5°C and the product is diazotized at this temperature by gradually adding 7.25 parts of nitrosylsulfuric acid (containing 13.1% of free dinitrogen trioxide). After stirring the mixture for one hour, 0.4 part of urea is added. The diazo solution thus obtained is allowed to run gradually into a solution consisting of 4.9 parts of N,N-di-($\beta$-hydroxyethyl)-3-methylaminobenzene, 500 parts of water, 3 parts of concentrated hydrochloric acid, 250 parts of sodium acetate and 200 parts of ice. The dye, obtained in a crystalline form, is filtered off after stirring for 1 hour, washed neutral with water and dried unter reduced pressure at 50°C. It dyes polyamide in brilliant blue hues.

EXAMPLE 6

If instead of the 7.75 parts of 2-amino-3,5-dibromobenzoic acid thioamide and 4.9 parts of N,N-di-($\beta$-hydroxyethyl)-3-methylamino-benzene, mentioned in Example 5, 6.9 parts of 2-amino-3-bromo-5-nitrobenzoic acid thioamide and 5.25 parts of N,N-dihydroxyethyl-N'-acetyl-m-phenylenediamine (calculated as 100% pure) are used and the batch is worked up as in Example 5, a greenish blue dye is obtained.

EXAMPLE 7

As a modification of Example 3, the same dye may also be prepared by effecting the oxidative ring closure by adding 3.4 parts of 50% strength hydrogen peroxide instead of by heating to 80°C. On adding the hydrogen peroxide dropwise, an exothermic reaction occurs, but the mixture should not heat up above 45°C and is cooled with an ice bath, if necessary. After all the hydrogen peroxide has been added, the mixture is stirred for a further hour and is then diazotized, coupled and worked up as described in Example 3. The dye is identical with that of Example 3.

EXAMPLE 8

7.75 parts of 2-amino-3,5-dibromobenzoic acid thioamide are introduced, whilst stirring, into 70 parts of concentrated sulfuric acid at room temperature. 3.5 parts of 30% strength hydrogen peroxide are added dropwise to this mixture, which is (initially) at room temperature, at a rate such that the temperature does not rise above 40°C. When all has been added, the mixture is stirred for a further 30 minutes and is then diazotized as described in Example 5. The resulting clear solution of the diazonium salt is stirred slowly into a solution consisting of 300 parts of water, 150 parts of ice, 1.5 parts of concentrated hydrochloric acid and 6 parts of 85.7% pure N,β-carbomethoxyethyl-N-ethylaniline (corresponding to 5.3 parts of 100% pure material). The mixture is stirred for a further 30 minutes at from 0° to 5°C and is then brought to pH 3 by dropwise addition of about 150 parts of 50% strength aqueous sodium hydroxide solution at the same temperature; it is then stirred for a further hour and the dye is filtered off, washed neutral with water and dried under reduced pressure at 50°C.

EXAMPLE 9

11.4 parts of peracetic acid (about 40% strength) are added dropwise to a solution of 9.85 parts of 5-nitro-2-aminobenzoic acid thioamide in 110 parts of sulfuric acid (96 to 98% strength) at such a rate that the temperature does not rise above 35°C. The mixture is then stirred for a further hour at 35°C and cooled to 0°C, and 10 parts of propionic acid are added dropwise, followed by 15 parts of nitrosylsulfuric acid (containing 12.8% of free dinitrogen trioxide), also added dropwise. The further reaction and working up are carried out as described in Example 4, and the same dye is isolated.

EXAMPLE 10

1.5 parts of potassium bromide are added, whilst stirring, to a solution of 9.85 parts of 5-nitro-2-aminobenzoic acid thioamide in 110 parts of 100% strength sulfuric acid at room temperature. An exothermic reaction occurs and the temperature rises to about 43°C. After all has been added, the mixture is stirred for a further 1.5 hours at 40°C and is then cooled to 0°C and treated as described in the above Example 9. The same dye is obtained.

EXAMPLE 11

9.85 parts of 5-nitro-2-aminobenzoic acid thioamide are gradually introduced into a solution of 1 part of bromine in 90 parts of 100% strength sulfuric acid and the mixture is then heated to from 40° to 45°C for 1½ hours. The solution is then cooled and reacted further as described in Example 10.

I claim:

1. In a process for the manufacture of 3-amino-2,1-benzisothiazoles of the formula

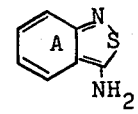

wherein the ring A is unsubstituted or substituted by chloro, bromo, nitro, $C_1$- to $C_4$-alkyl, benzyl, phenyl, amino, $C_1$- to $C_4$-alkylamino or -dialkylamino, phenylamino, acetyl, benzoyl, hydroxy, methoxy, ethoxy, phenoxy, sulfamoyl, $C_1$- to $C_4$-mono- or di-alkyl-substituted sulfamoyl, phenylsulfamoyl, methylsulfonyl, ethylsulfonyl or phenylsulfonyl, by oxidative ring closure of a thioamide of the formula

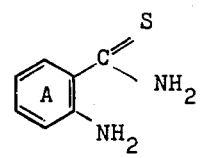

the improvement which comprises effecting the ring closure in about 85 to 110% sulfuric acid at temperatures of about 10° to 160°C.

2. The process according to claim 1 using 95 to 102% sulfuric acid.

3. The process according to claim 1 using a temperature between 40° and 90°C.

4. The process according to claim 1 wherein a catalytic amount of bromine is added to accelerate the reaction.

5. The process according to claim 1 using a 3 to 15-fold amount of sulfuric acid based on the weight of thioamide.

6. The process according to claim 1 using a 95 to 102% sulfuric acid in an amount of about 3 to 15 times the amount by weight of the thioamide and using a temperature of between 40° and 90°C.

7. The process according to claim 1 using a 96 to 100% sulfuric acid and a temperature of 60° to 100°C., the ring closure reaction being maintained for about 1 to 5 hours.

8. The process according to claim 1 wherein an oxidizing agent is added to the sulfuric acid reaction medium to accelerate the ring closure and the reaction is carried out at a temperature of about 10° to 60°C.

9. The process according to claim 8 using a temperature of about 20° to 45°C.

10. The process according to claim 8 using an added oxidizing agent selected from the group consisting of hydrogen peroxide, peracetic acid, perbenzoic acid, perphthalic acid, sulfuryl chloride and bromine.

* * * * *